United States Patent
Hanson et al.

(10) Patent No.: US 12,146,191 B1
(45) Date of Patent: Nov. 19, 2024

(54) DETECTION AND CLASSIFICATION OF IMP CARBAPENEMASES USING REAL-TIME POLYMERASE CHAIN REACTION ASSAY

(71) Applicant: Creighton University, Omaha, NE (US)

(72) Inventors: Nancy D. Hanson, Omaha, NE (US); Hayden Smith, Beaverton, OR (US); Stacey Morrow, Omaha, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 18/311,703

(22) Filed: May 3, 2023

Related U.S. Application Data (62) Division of application No. 16/794,754, filed on Feb. 19, 2020, now abandoned.

(60) Provisional application No. 62/807,328, filed on Feb. 19, 2019.

(51) Int. Cl.
*C12Q 1/6876* (2018.01)
*C12Q 1/34* (2006.01)

(52) U.S. Cl.
CPC ............ *C12Q 1/6876* (2013.01); *C12Q 1/34* (2013.01)

(58) Field of Classification Search
None
See application file for complete search history.

(56) References Cited

FOREIGN PATENT DOCUMENTS

WO   WO 2018/232028   * 12/2018

OTHER PUBLICATIONS

Smith (OFID 2014:4 (Suppl 1) S591 Poster Abstract).*
Hayden Z. Smith, Nancy D. Hanson, PhD; "Impmetallo-β-Lactamase Detection RT-PCR Assay Using a Bioinformatic Approach Forclinical Application", Department of Medical Microbiology and Immunology, Creighton University School of Medicine, Omaha NE; Oct. 7, 2017.
Navarro (Clinica Chimica Acta 439 (2015) pp. 231-250).

* cited by examiner

*Primary Examiner* — Amanda Haney
(74) *Attorney, Agent, or Firm* — Mallory M. Henninger; Advent, LLP (57) ABSTRACT

Systems and methods for detection and classification of IMP carbapenemases are described. In an aspect, sets of PCR primers associated with specific probes can be used to identify specific families of IMP β-lactamases and utilize multiple primer sets to identify all IMP variants via real-time PCR assays. The sets of PCR primers can also be coupled with a fluorescent dye to detect a broad range of the IMP variants.

10 Claims, 8 Drawing Sheets

Specification includes a Sequence Listing.

FIG. 1

FIRST MIXTURE PROBES

| Probe Name | Probe Composition | Sequence ID Number |
|---|---|---|
| 1.1 | 5'-/56-FAM/ CGTAGTGGTTTGG(C/T)TACCTGAAAA /3IABkFQ/-3' | SEQ ID NO:7 |
| 1.2 | 5'-/5TEX615/ AAGCTTGAAGAAGGTGTTTTGTTCAT /3IAbRQSp/-3' | SEQ ID NO:8 |
| 1.3 | 5'-/5HEX/ CCCACGTATGGGTCTGAATTAAC /3IABkFQ/-3' | SEQ ID NO:9 |

FIG. 2A

SECOND MIXTURE PROBES

| Probe Name | Probe Composition | Sequence ID Number |
|---|---|---|
| 2.1 | 5'-/5HEX/ AAATATGGTAAGGCAAAACTGGTTG/ 3IABkFQ/-3' | SEQ ID NO:16 |
| 2.2 | 5'-/5TEX615/ GGAATAGAGTGGCTTAATTCTCAAT /3IAbRQSp/-3' | SEQ ID NO:17 |
| 2.3 | 5'-/56-FAM/ TCAAAGGCAGTATTTCCTCACATTT /3IABkFQ/-3' | SEQ ID NO:18 |

DETECTION AND CLASSIFICATION OF IMP CARBAPENEMASES USING REAL-TIME POLYMERASE CHAIN REACTION ASSAY

INCORPORATION OF SEQUENCE LISTING

The sequence listing contained in the file named "Replacement_Sequence_Listing_ST26_12212023.xml", which is 23.6 kilobytes in size (measured in MS-Windows®), contains 18 sequences, and which was created on Dec. 21, 2023, is contemporaneously filed with this specification by electronic submission (using the United States Patent Office EFS-Web filing system) and is incorporated herein by reference in its entirety.

BACKGROUND

Bacterial infections are often treated with one or more types of antibiotics designed to kill or otherwise inhibit activity of bacteria. Certain types of bacteria, such as gram-negative bacteria, are particularly resistant to various antibiotic treatments. Gram-negative bacterial resistance to antibiotics has decreased the ability of health care professionals to combat infection. However, carbapenems are a class of drugs developed to combat drug-resistant bacteria and are the most potent β-lactam antibiotic for resistant bacteria. Carbapenemase-producing bacteria inactivate the carbapenem class of antibiotic resulting in a carbapenem-resistant phenotype. There are several types of carbapenemases including KPCs, OXAs, VIMs, NDMs, and IMPs. However, the IMP family of β-lactamases is the most genetically variable and difficult to detect using molecular techniques.

SUMMARY

Systems and methods for detection and classification of IMP carbapenemases are described. In an aspect, sets of PCR primers associated with specific probes can be used to identify specific families of IMP β-lactamases and utilize multiple primer sets to identify all IMP variants via real-time PCR assays. The sets of PCR primers can also be coupled with a fluorescent dye to detect a broad range of the IMP variants.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. In the figures, the use of the same reference numbers in different instances in the description and the figures may indicate similar or identical items.

DETAILED DESCRIPTION

Overview

Figure 1:
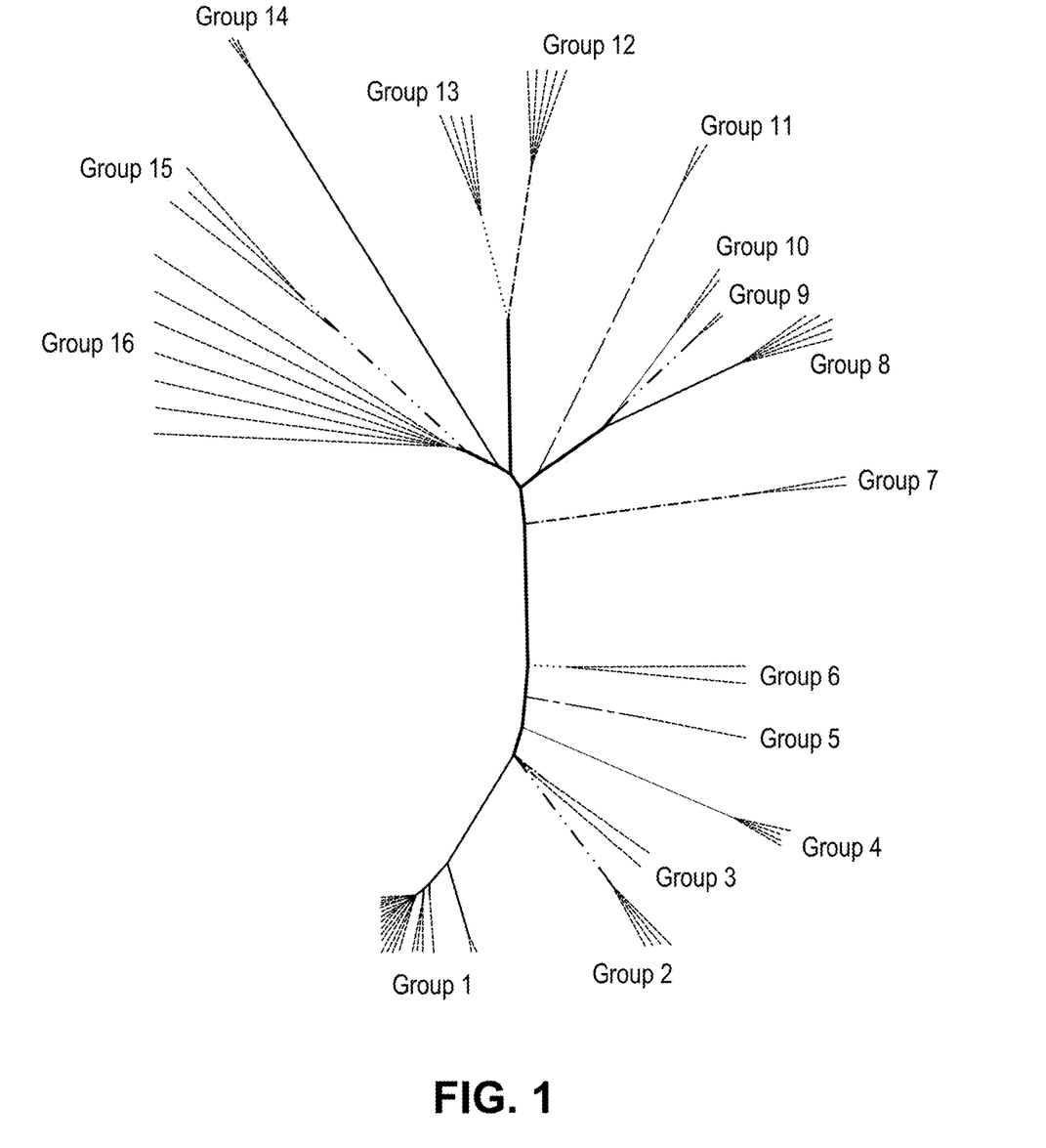
FIG. 1 is an illustration of an unrooted tree of genetic variants of the IMP carbapenemase family separated into sixteen groups representing 71 unique IMP variants in accordance with an example implementation of the present disclosure.

Carbapenem antibiotics are the drug of choice for most gram-negative multi-drug resistant bacterial infections. Bacterial resistance to carbapenem antibiotics began occurring in the early 1980s, showing as IMP-1 pseudomonas. In the early 1990s, carbapenem-degrading enzymes ("carbapenemases") were discovered in Enterobacteriaceae. Currently, many different types of carbapenemases are observed, including KPCs, OXAs, VIMs, NDMs, and IMPs. Many carbapenemases are encoded on and transmissible by plasmids. Traditionally, IMP type carbapenemases have been the most difficult type to classify due to the vast genetic diversity between different strains of IMP. For example, FIG. 1 illustrates an IMP gene tree broken into 16 genetically similar family groups representing over 70 unique IMP variants, with additional IMP alleles currently being discovered. Table 1 provides a listing of each IMP variant present in the groups shown in FIG. 1.

TABLE 1

| | IMP Variant Numbers |
|---|---|
| Group 1 | 78, 80, 77, 10, 40, 61, 30, 55, 60, 1, 42, 66, 52, 76, 6, 34, 3, 79, 70, 59, 4, 26, 38 |
| Group 2 | 43, 7, 73, 51 |
| Group 3 | 5, 28 |
| Group 4 | 25, 53, 45, 9 |
| Group 5 | 29 |
| Group 6 | 62, 15 |
| Group 7 | 12, 63 |
| Group 8 | 11, 21, 68, 41, 44 |
| Group 9 | 22, 58 |
| Group 10 | 74, 16 |
| Group 11 | 35, 31 |
| Group 12 | 71, 75, 49, 18, 56 |
| Group 13 | 48, 14, 32, 54 |
| Group 14 | 64, 27, 67 |

TABLE 1-continued

| | IMP Variant Numbers |
|---|---|
| Group 15 | 13, 37, 33 |
| Group 16 | 23, 47, 8, 24, 20, 2, 19 |

The IMP family of β-lactamases is the most genetically variable and difficult to detect using molecular techniques. Current methods of IMP detection are unsuitable for broad IMP gene detection with due in part to the vast genetic variability of the IMP family. As such, current methods of IMP detection insufficient to detect all IMP genes associated with gram-negative infections, which negatively impacts antibiotic stewardship and infection control efforts in hospital and community settings.

Accordingly, the present disclosure is directed, at least in part, to systems and methods for detection and classification of IMP carbapenemases using real time polymerase chain reaction (RT-PCR) techniques. In implementations, the systems and methods utilize a specific set of PCR primers associated with a specific probe to identify specific families of IMP β-lactamases and utilize multiple primer sets to identify all IMP variants. The set of PCR primers can also be coupled with a fluorescent dye to detect a broad range of the IMP variants. For example, the specific probes mixed with primer sets can bind to specific families of IMP variants via probe binding for replication by the PCR primers to identify the specific families of IMP variants, whereas the multiple primer sets mixed with fluorescent dye can detect any IMP variant in a Gram-negative organism, but may not differentiate to which family the gene belongs based on fluorescence alone. Example implementations of detection and classification of IMP carbapenemases using RT-PCR techniques are described further herein.

Example Implementations

First RT-PCR Composition

In implementations, detection and classification of multiple specific families of IMP variants is facilitated by a first composition including a group of primer sets and a group of probes for use in RT-PCR techniques. The first composition includes two separate mixtures of primer sets and probes. For example, the first composition can include a first mixture including three primer sets (e.g., one forward primer, one reverse primer) and three probes and can include a second mixture including three different primer sets (e.g., one forward primer, one reverse primer) and three different probes. In implementations, the primers of the first mixture are presented in Table 2, where the primer name includes the following naming convention: [mixture number].[primer set number].[forward(1) or reverse (2) primer]:

TABLE 2

| Primer Name | Primer Composition | Sequence ID Number |
|---|---|---|
| 1.1.1 | 5'-ACGGGTGGAATAGAGTGGC-3' | SEQ ID NO: 1 |
| 1.1.2 | 5'-GCGGACTTTGGCCAAGCTT-3' | SEQ ID NO: 2 |
| 1.2.1 | 5'-GTAGCATTACTGCCGCAGG-3' | SEQ ID NO: 3 |
| 1.2.2 | 5'-TAACCGCGCTCCACAAACC-3' | SEQ ID NO: 4 |

TABLE 2-continued

| Primer Name | Primer Composition | Sequence ID Number |
|---|---|---|
| 1.3.1 | 5'-GGGCGGAATAGAGTGGCTT-3' | SEQ ID NO: 5 |
| 1.3.2 | 5'-TTTGGCGGACTCTGGCCAA-3' | SEQ ID NO: 6 |

Figure 2A:
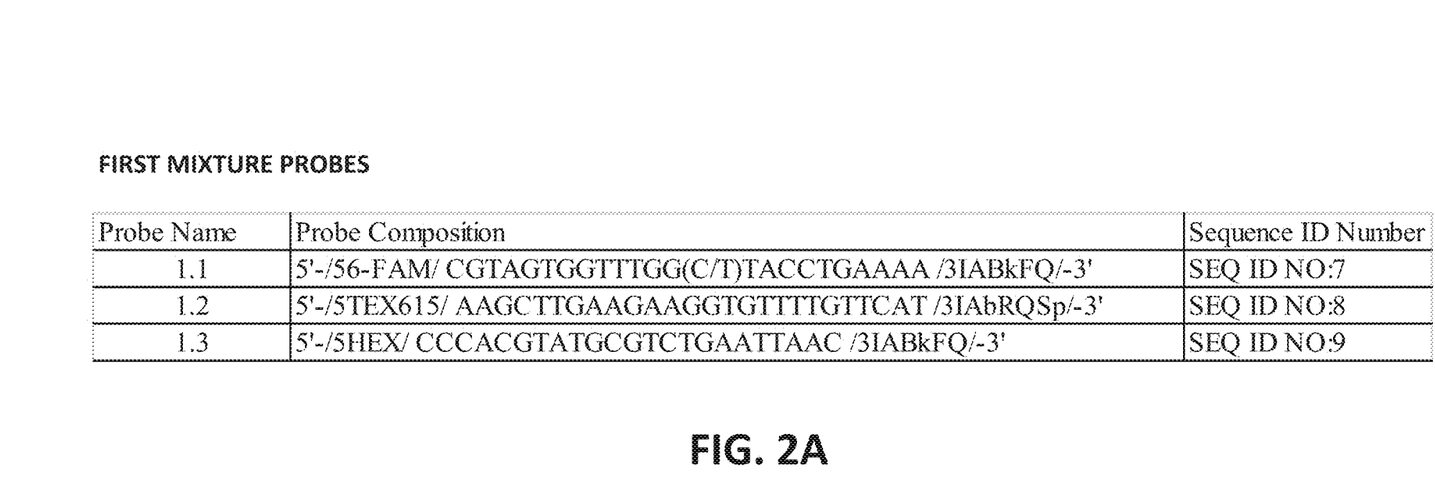
FIG. 2A is a table of compositions of probes for a first mixture to assay IMP carbapenemases in accordance with an example implementation of the present disclosure.

In implementations, the probes of the first mixture are presented in FIG. 2A, where the probe name includes the following naming convention: [mixture number].[probe number]. In implementations, the primers of the second mixture are presented in Table 3, where the primer name includes the following naming convention: [mixture number].[primer set number].[forward(1) or reverse (2) primer]:

TABLE 3

| Primer Name | Primer Composition | Sequence ID Number |
|---|---|---|
| 2.1.1 | 5'-GAAGCTTGGCCAAAGTCCG-3' | SEQ ID NO: 10 |
| 2.1.2 | 5'-ACCCTTTAACCGCCTGCTC-3' | SEQ ID NO: 11 |
| 2.2.1 | 5'-CACGGCTTGGTGGTTCTTG-3' | SEQ ID NO: 12 |
| 2.2.2 | 5'-CGTTATCTGGAGTGTGCCC-3' | SEQ ID NO: 13 |
| 2.3.1 | 5'-CACGGCTTGGTGGTTCTTG-3' | SEQ ID NO: 14 |
| 2.3.2 | 5'-TATCCTGAGTGTGCCCTGG-3' | SEQ ID NO: 15 |

Figure 2B:
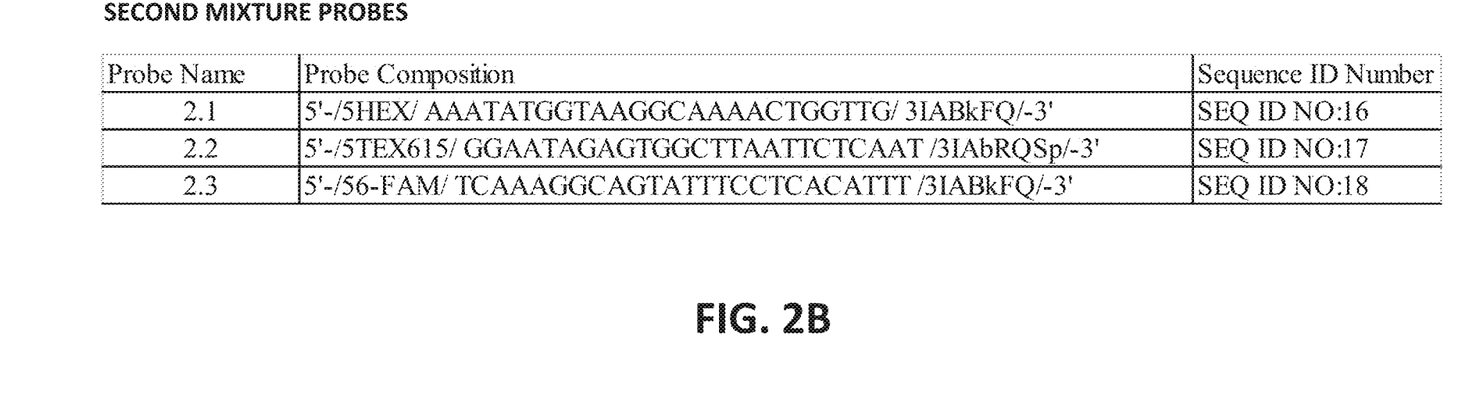
FIG. 2B is a table of compositions of probes for a first mixture to assay IMP carbapenemases in accordance with an example implementation of the present disclosure.

In implementations, the probes of the second mixture are presented in FIG. 2B, where the probe name includes the following naming convention: [mixture number].[probe number].

The first composition also includes reagents to facilitate the RT-PCR analyses. For example, the first mixture of the first composition can include, in addition to the primer sets and probes, water, a buffer solution (e.g., FB I buffer solution), nucleotides, internal control (IC) primers and probe, a PCR enzyme (e.g., PhilisaFast™ DNA polymerase), and DNA template. In an implementation, the first mixture of the first composition is shown in Table 4, with the primers having a premixed concentration of 100 µM (for a final mix concentration of 0.2 µM), and with the probes having a premixed concentration of 5 µM (for a final mix concentration of 0.1 µM):

TABLE 4

| Component | Vol. Per Reaction |
|---|---|
| Water | 16.85 |
| FB I (10x) | 2.50 |
| 2.5 mM dNTP | 2.00 |
| 1.1.1 Primer | 0.05 |
| 1.1.2 Primer | 0.05 |
| 1.1 Probe | 0.50 |
| 1.2.1 Primer | 0.05 |
| 1.2.2 Primer | 0.05 |
| 1.2 Probe | 0.50 |
| 1.3.1 Primer | 0.05 |
| 1.3.2 Primer | 0.05 |
| 1.3 Probe | 0.50 |
| IC F' | 0.05 |
| IC R' | 0.05 |

TABLE 4-continued

| Component | Vol. Per Reaction |
| --- | --- |
| IC TYE | 0.50 |
| PhilisaFast | 0.25 |
| DNA | 1.00 |
| Final Volume | 25.00 |

As another example, the second mixture of the first composition can include, in addition to the primer sets and probes, water, a buffer solution (e.g., FB I buffer solution), nucleotides, internal control (IC) primers and probe, an RT-PCR enzyme (e.g., PhilisaFast™ DNA polymerase), and DNA template. In an implementation, the second mixture of the first composition is shown in Table 5, with the primers having a premixed concentration of 100 µM (for a final mix concentration of 0.2 µM), and with the probes having a premixed concentration of 2.5 µM (for a final mix concentration of 0.05 µM):

TABLE 5

| Component | Vol. Per Reaction |
| --- | --- |
| Water | 16.85 |
| FB I (10x) | 2.50 |
| 2.5 mM dNTP | 2.00 |
| 2.1.1 Primer | 0.05 |
| 2.1.2 Primer | 0.05 |
| 2.1 Probe | 0.50 |
| 2.2.1 Primer | 0.05 |
| 2.2.2 Primer | 0.05 |
| 2.2 Probe | 0.50 |
| 2.3.1 Primer | 0.05 |
| 2.3.2 Primer | 0.05 |
| 2.3 Probe | 0.50 |
| IC F' | 0.05 |
| IC R' | 0.05 |
| IC TYE | 0.50 |
| PhilisaFast | 0.25 |
| DNA | 1.00 |
| Final Volume | 25.00 |

The first mixture and the second mixture of the first composition can be introduced to an automated RT-PCR instrument having cycling conditions to amplify differing IMP variants. For example, the first composition can be utilized with an assay to have an annealing temperature of about 60° C. and an elongation temperature of about 72° C. The cycling conditions including the temperatures and durations of each cycle can vary depending on the desired amplification progressions. In an implementation, the cycling conditions for each of the first mixture and the second mixture of the first composition includes one cycle of at a temperature of about 98° C. for about 30 seconds followed by 30 cycles having a first duration of about 5 seconds at a temperature of about 98° C., a second duration of about 10 seconds at a temperature of about 60° C., and a third duration of about 20 seconds at a temperature of about 72° C.

The first composition can be utilized to identify many specific IMP alleles following the RT-PCR treatments. For example, a breakdown of specific IMP alleles identified by different primer sets and probes is provided in Table 6:

TABLE 6

| Primers | Probe | IMP Variants |
| --- | --- | --- |
| 1.1.1 & 1.1.2 | 1.1 | 9, 12, 14, 18, 25, 32, 45, 48, 49, 54, 56 |
| 1.2.1 & 1.2.2 | 1.2 | 8, 11, 13, 15, 16, 19, 20, 21, 24, 33, 37, 41, 47 |
| 1.3.1 & 1.3.2 | 1.3 | 1, 2, 5, 6, 8, 10, 15, 19, 20, 24, 27, 28, 30, 40, 42, 47, 52, 55 |
| 2.1.1 & 2.1.2 | 2.1 | 1, 3, 4, 6, 10, 18, 26, 30, 34, 38, 40, 42, 49, 52, 55, 56 |
| 2.2.1 & 2.2.2 | 2.2 | 2, 5, 7, 8, 9, 11, 14, 15, 19, 20, 21, 24, 25, 28, 29, 32, 41, 45, 47, 48, 51, 54 |
| 2.3.1 & 2.3.2 | 2.3 | 11, 14, 21, 31, 32, 35, 41, 48, 54 |

Second RT-PCR Composition

In implementations, detection of multiple specific families of IMP variants is facilitated by a second composition including a group of primer sets and a fluorescent dye for use in RT-PCR techniques. The second composition includes two separate mixtures of primer sets each with a fluorescent dye. In implementations, the second composition is similar to the first composition, however instead of including specific probes for specific IMP allele detection and classification, the second composition includes a fluorescent dye for IMP detection. For example, the second composition can include a first mixture including three primer sets (e.g., one forward primer, one reverse primer) and a fluorescent dye and can include a second mixture including three different primer sets (e.g., one forward primer, one reverse primer) and a fluorescent dye. In implementations, the primers of the first mixture of the second composition are the same as those provided in the first mixture of the first composition (e.g., those presented in Table 2) and the fluorescent dye includes EvaGreen™ dye. The second mixture of the second composition can be the same as those provided in the second mixture of the first composition (e.g., those presented in Table 3) and the fluorescent dye includes EvaGreen™ dye.

The second composition also includes reagents to facilitate RT-PCR analyses. For example, the first mixture of the second composition can include, in addition to the primer sets and fluorescent dye, water, a buffer solution (e.g., 10× Taq buffer), a salt (e.g., 25 mM MgCl$_2$), nucleotides, a PCR enzyme (e.g., Taq polymerase), and DNA template. In an implementation, the first mixture of the second composition is shown in Table 7, with the primers having a premixed concentration of 100 µM (for a final mix concentration of 0.2 µM):

TABLE 7

| Component | Vol. Per Reaction |
| --- | --- |
| Water | 18.57 |
| Taq Buffer (10x) | 2.50 |
| 25 mM MgCl2 | 1.25 |
| 10 mM dNTP | 0.50 |
| 20x EvaGreen dye | 0.63 |
| 1.1.1 Primer | 0.05 |
| 1.1.2 Primer | 0.05 |
| 1.2.1 Primer | 0.05 |
| 1.2.2 Primer | 0.05 |
| 1.3.1 Primer | 0.05 |
| 1.3.2 Primer | 0.05 |
| Taq Polymerase | 0.25 |
| DNA | 1.00 |
| Final Volume | 25.00 |

As another example, the second mixture of the second composition can include, in addition to the primer sets and fluorescent dye, water, a buffer solution (e.g., 10× Taq buffer), a salt (e.g., 25 mM MgCl$_2$), nucleotides, a PCR enzyme (e.g., Taq polymerase), and DNA template. In an implementation, the second mixture of the second composition is shown in Table 8, with the primers having a premixed concentration of 100 µM (for a final mix concentration of 0.2 µM):

TABLE 8

| Component | Vol. Per Reaction |
|---|---|
| Water | 18.57 |
| Taq Buffer (10x) | 2.50 |
| 25 mM MgCl2 | 1.25 |
| 10 mM dNTP | 0.50 |
| 20x EvaGreen dye | 0.63 |
| 2.1.1 Primer | 0.05 |
| 2.1.2 Primer | 0.05 |
| 2.2.1 Primer | 0.05 |
| 2.2.2 Primer | 0.05 |
| 2.3.1 Primer | 0.05 |
| 2.3.2 Primer | 0.05 |
| Taq Polymerase | 0.25 |
| DNA | 1.00 |
| Final Volume | 25.00 |

The first mixture and the second mixture of the second composition can be introduced to an automated RT-PCR instrument having cycling conditions to amplify differing IMP variants. For example, the second composition can be utilized with an assay to have an annealing temperature of about 60° C. and an elongation temperature of about 72° C. The cycling conditions including the temperatures and durations of each cycle can vary depending on the desired amplification progressions. In an implementation, the cycling conditions for each of the first mixture and the second mixture of the second composition includes one cycle of at a temperature of about 98° C. for about 30 seconds followed by 25 cycles having a first duration of about 30 seconds at a temperature of about 98° C., a second duration of about 30 seconds at a temperature of about 60° C., and a third duration of about 30 seconds at a temperature of about 72° C.

Primer Set and Probe Development Methods

Genetically similar variants of IMP β-lactamases were grouped together to determine a grouping of primers that could detect a wide range of different variants of the IMP β-lactamase family. In an implementation, computer simulation was utilized to group genetically similar variants of IMP β-lactamases, where genetic similarity was defined as being within 0.05 Robinson-Foulds tree distances. The genetic similarity was verified with RAxML tree analysis. Of the 71 unique IMP variants, the IMP gene tree was broken into 16 genetically similar families (e.g., shown as groups in FIG. 1 and described herein above). Seven of the 16 families were tested, with representative families chosen due to genetic diversity, and with uniqueness of a family being defined by computer simulation and laboratory experiment. The IMP variants tested included IMP1, IMP4, IMP7, IMP8, IMP14, IMP18, IMP27, and IMP35, which correspond to groups 1, 1, 2, 16, 13, 12, 14, and 11, respectively, shown in FIG. 1.

The primers for the first composition and the second composition were selected on the basis of a plurality of factors to detect the variants from the respective genetically diverse families. In an implementation, the factors of the primers included an annealing temperature of about 57° C., a primer length from about 18 base pairs (bp) to about 21 bp, and amplicon length from about 50 bp to about 2000 bp, a first mutation factor where no mutation allowed in the first 6 nucleotides of the upstream 3' region of the primer, and a second mutation factor where a maximum of one mutation is permitted outside the upstream 3' region of the primer. The primers provided in Tables 2 and 3 are examples of primers found to satisfy these factors. Additional primers may also satisfy these factors within the scope of the present disclosure.

The probes for the first composition were selected on the basis of a plurality of factors to assist in classification of the specific IMP variants. In an implementation, the factors of the probes included an annealing temperature from about 65° C. to about 70° C., a probe length from about 22 bp to about 28 bp, a position factor where the probe sits at least 10 bp away from the primer position, a first mutation factor where no mutation is present on the first and last flanking 8 bp of the probe, and a second mutation factor where a maximum of one mutation is permitted in the inner probe sequence. The probes provided in FIGS. 2A and 2B are examples of probes found to satisfy these factors. Additional probes may also satisfy these factors within the scope of the present disclosure.

The first composition was determined to identify the specific IMP alleles provided in Table 6, where empirical validation was achieved using DNA templates for IMP1, IMP4, IMP7, IMP8, IMP14, IMP18, IMP27, and IMP35. The DNA templates were generated from eight different clinical isolates to produce the different IMP β-lactamases types using a boil-prep method. The isolates carrying the represented IMP genes included *E. coli*, *Pseudomonas aeruginosa*, *Klebsiella* spp., *Proteus* spp., and *Enterobacter* spp.

IMP Detection and Classification Assay

Figure 3:
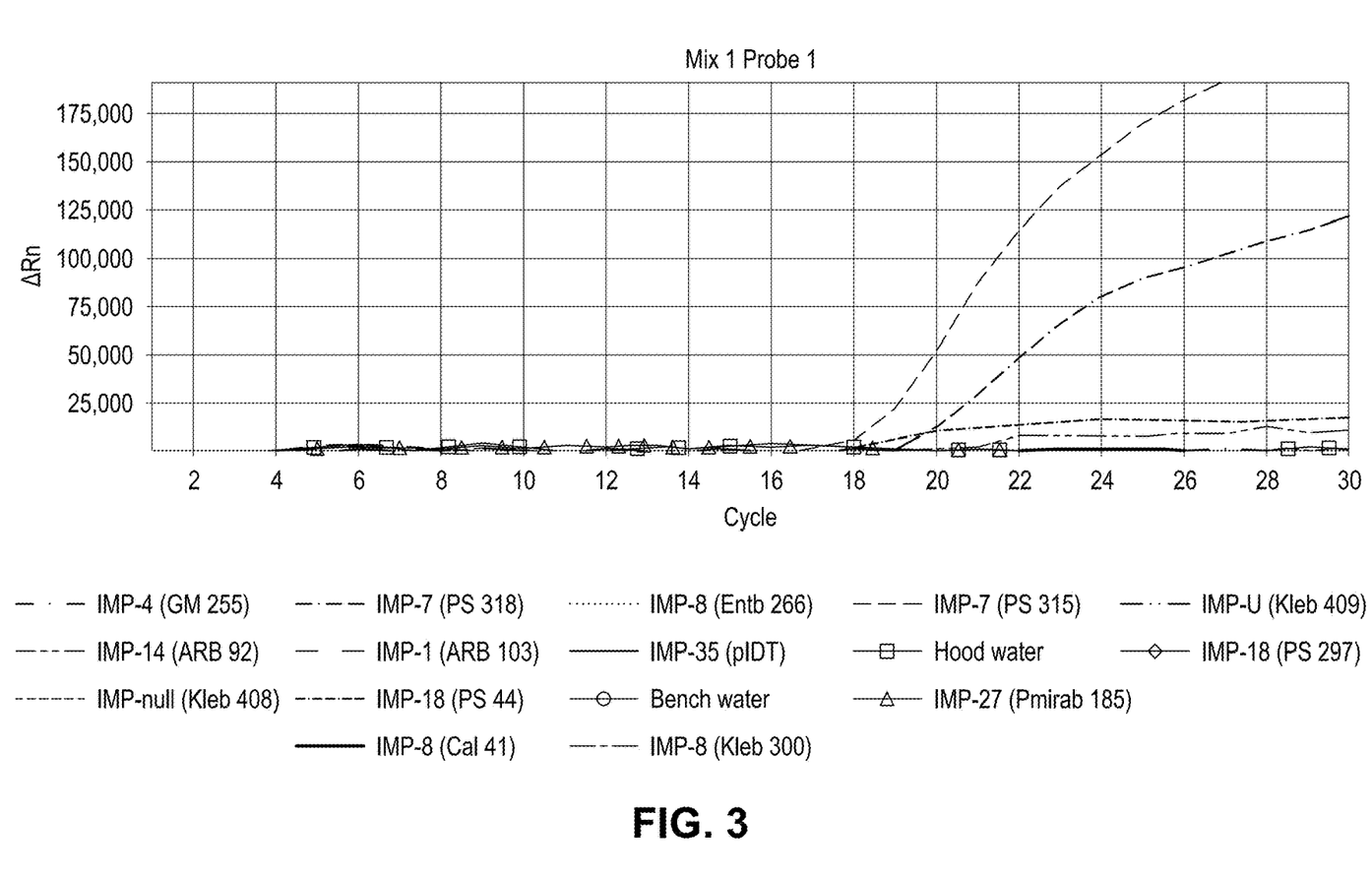
FIG. 3 is a chart of RT-PCR results associated with a first probe of a first mixture to assay IMP carbapenemases in accordance with an example implementation of the present disclosure.
Figure 4:
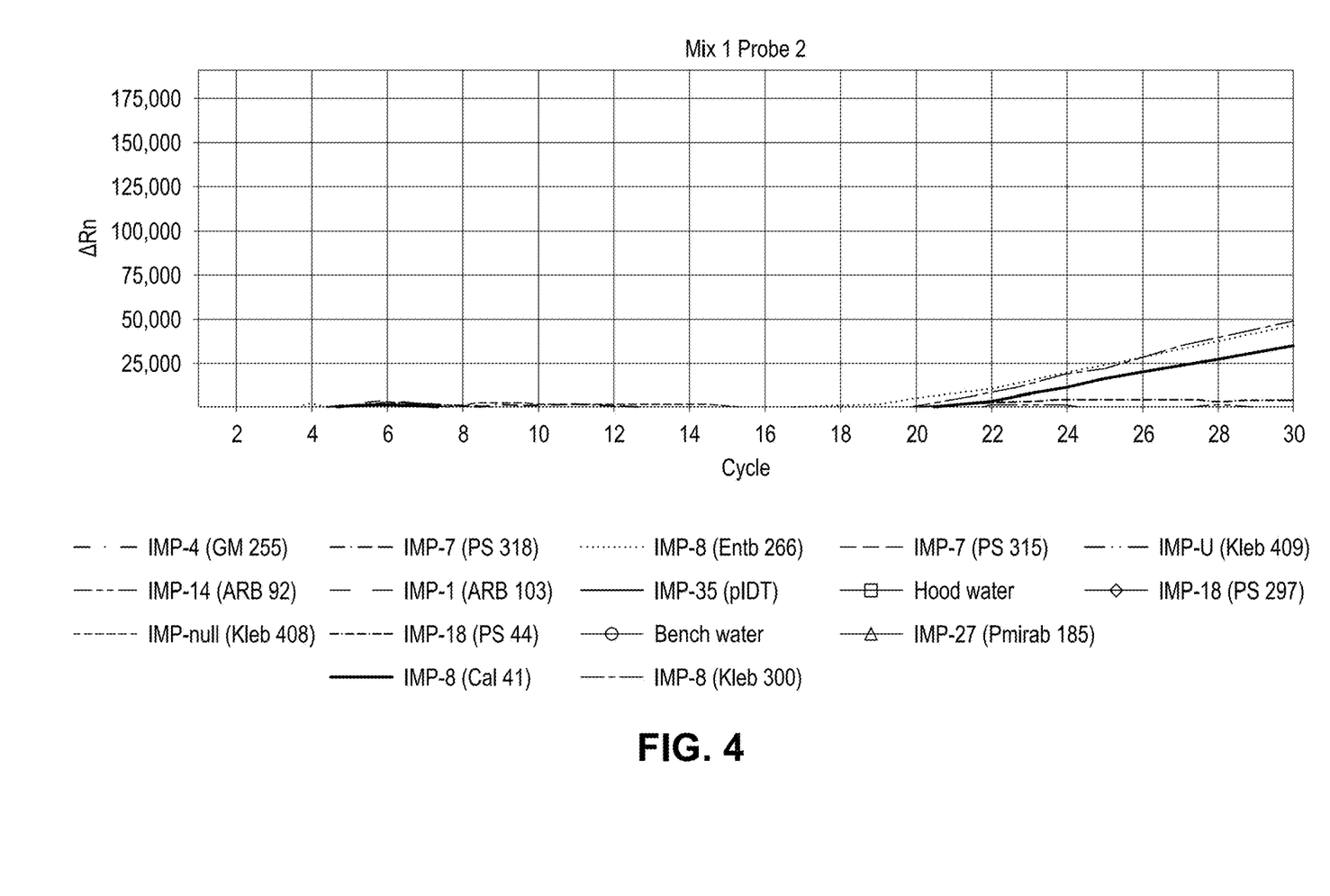
FIG. 4 is a chart of RT-PCR results associated with a second probe of a first mixture to assay IMP carbapenemases in accordance with an example implementation of the present disclosure.
Figure 5:
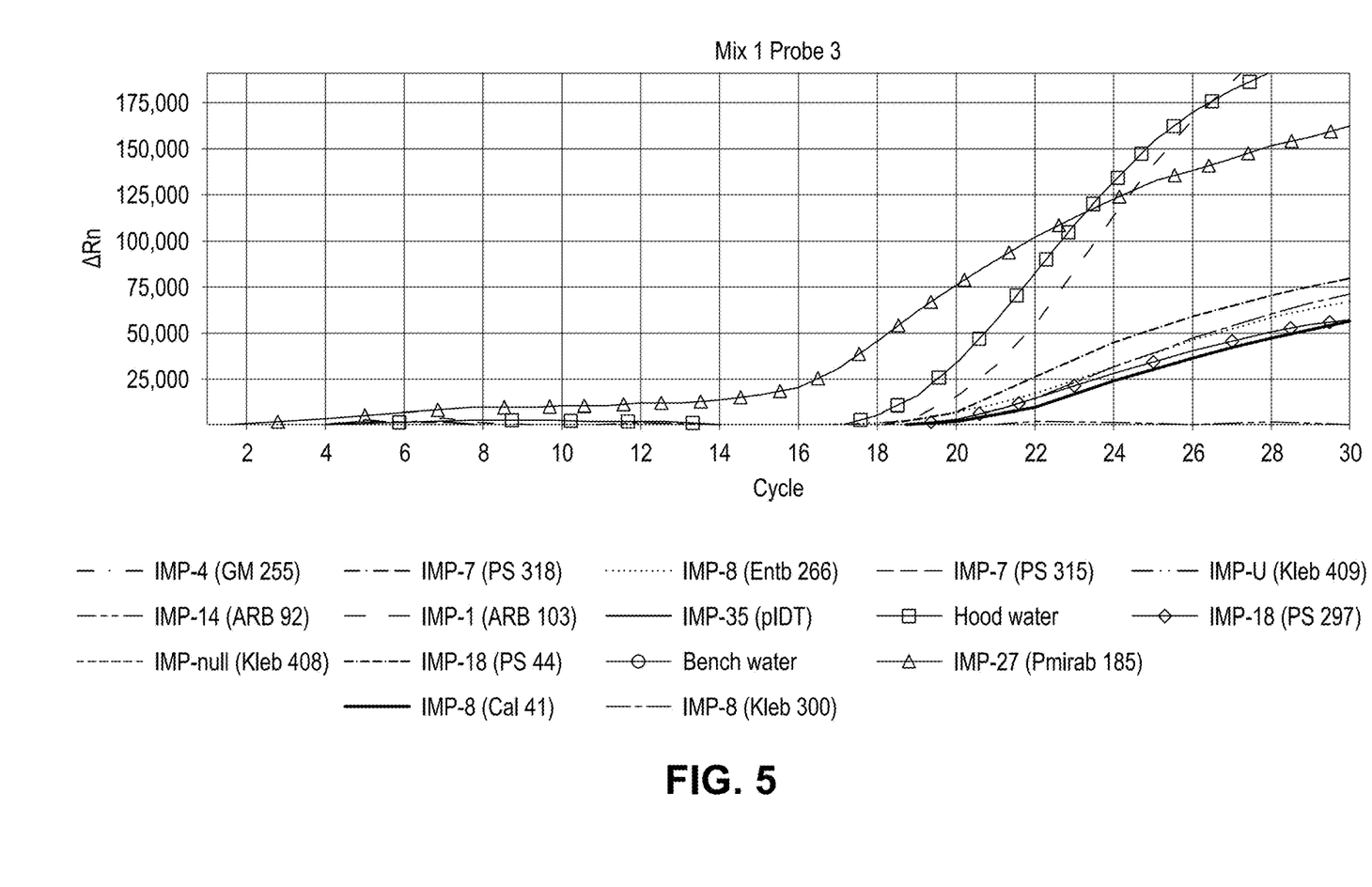
FIG. 5 is a chart of RT-PCR results associated with a third probe of a first mixture to assay IMP carbapenemases in accordance with an example implementation of the present disclosure.
Figure 6:
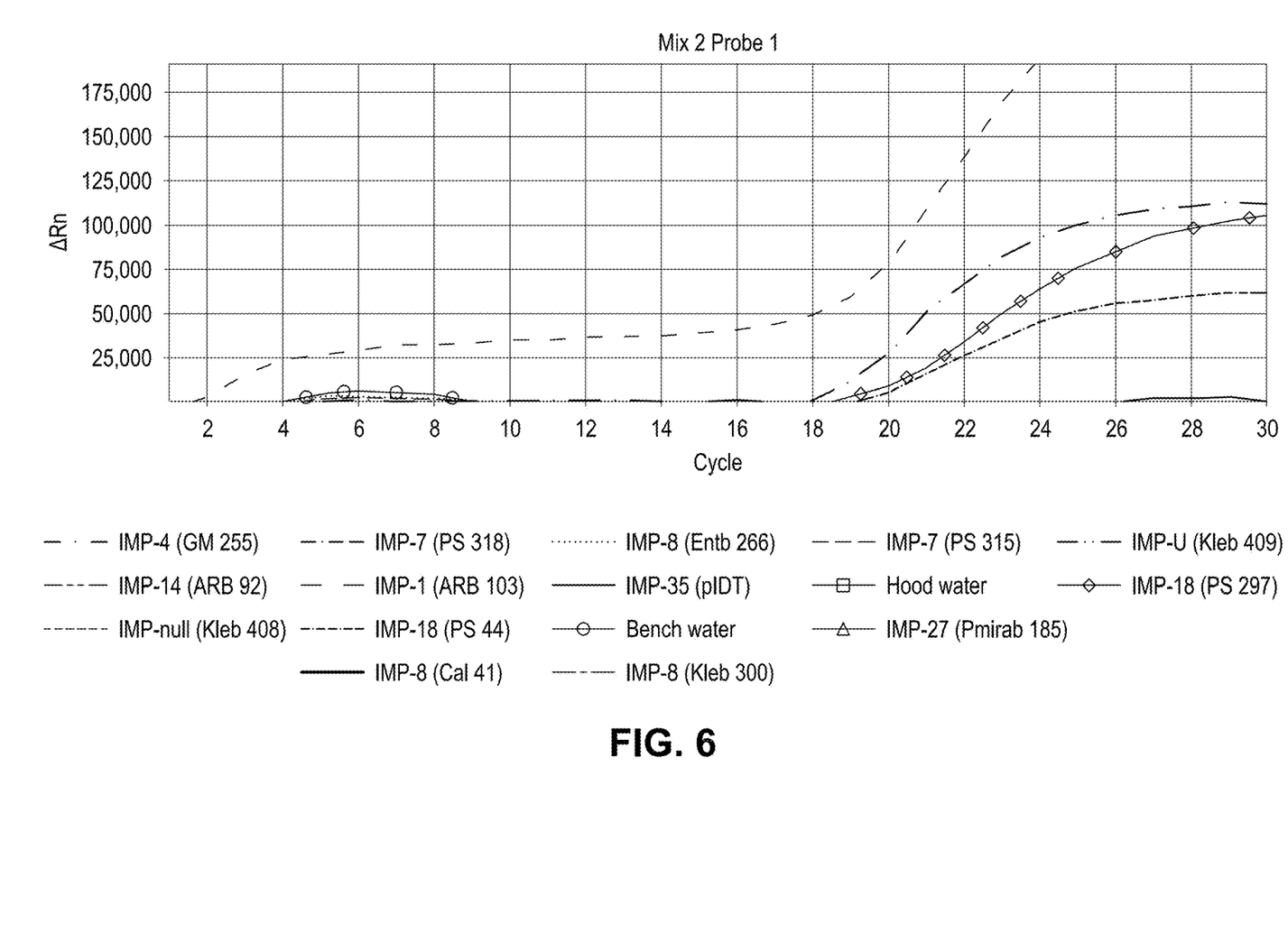
FIG. 6 is a chart of RT-PCR results associated with a fourth probe of a second mixture to assay IMP carbapenemases in accordance with an example implementation of the present disclosure.
Figure 7:
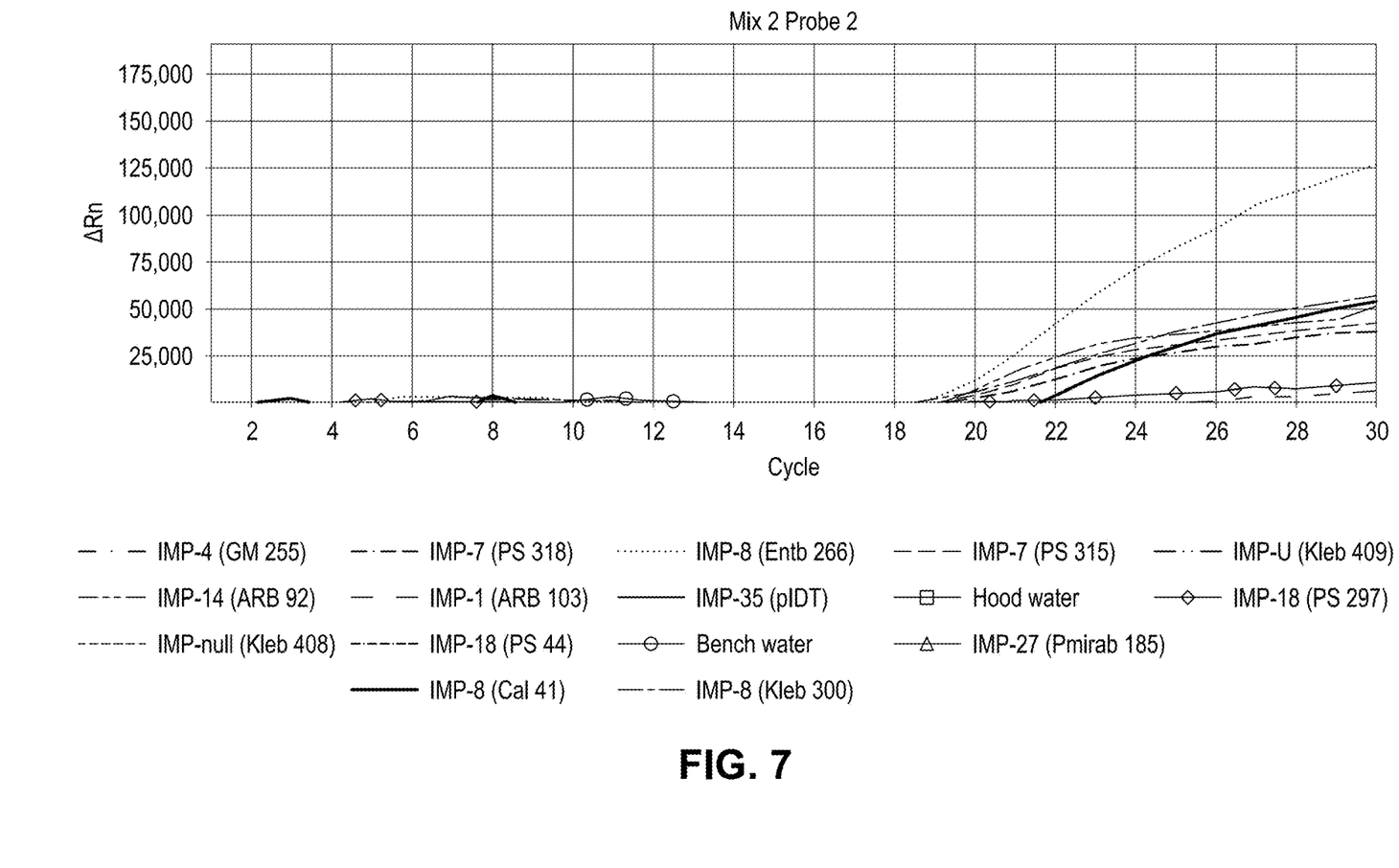
FIG. 7 is a chart of RT-PCR results associated with a fifth probe of a second mixture to assay IMP carbapenemases in accordance with an example implementation of the present disclosure.
Figure 8:
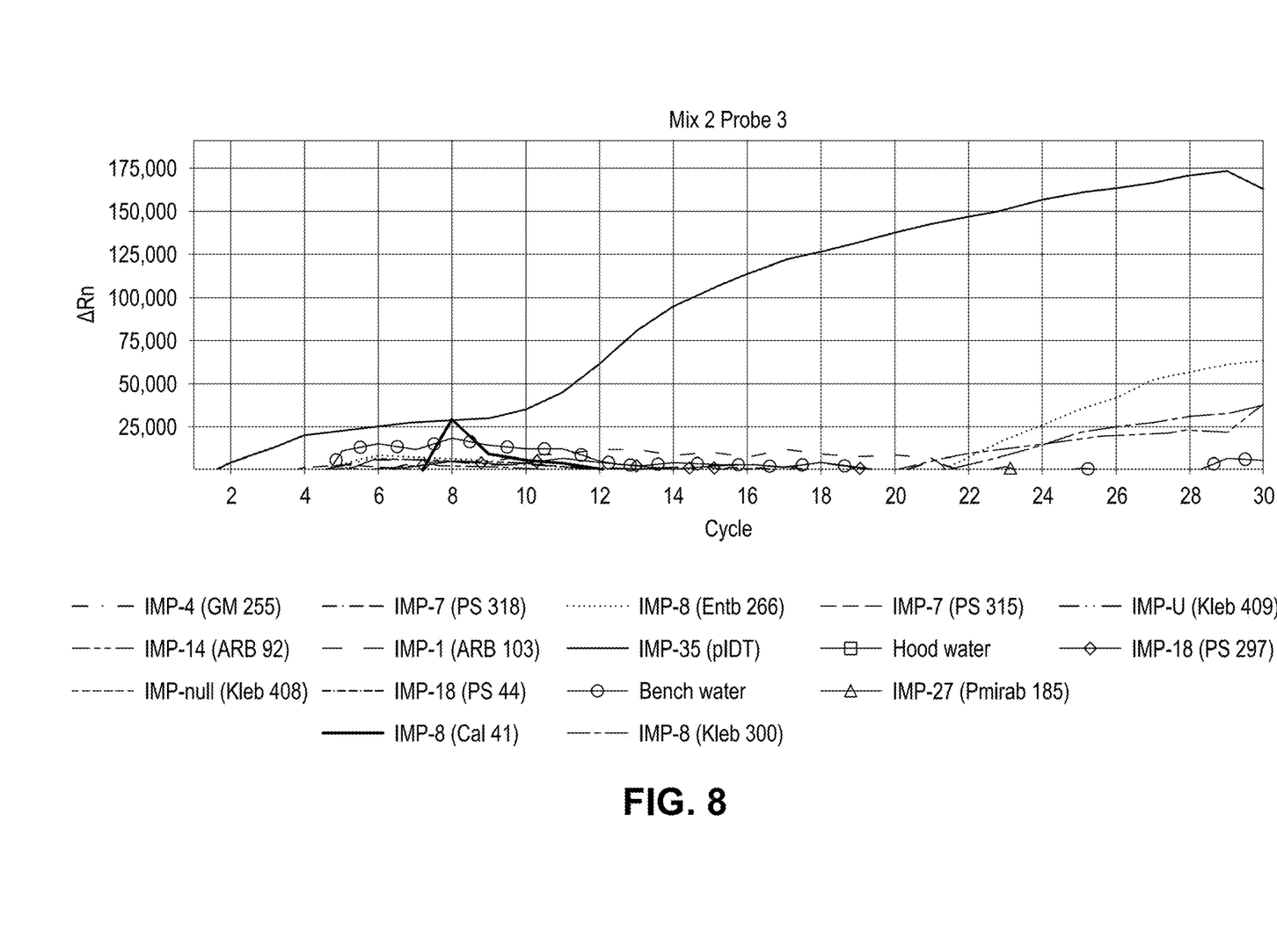
FIG. 8 is a chart of RT-PCR results associated with a sixth probe of a second mixture to assay IMP carbapenemases in accordance with an example implementation of the present disclosure.

A real time polymerase chain reaction (RT-PCR) assay was performed to analyze the detection and classification performance of the first composition using thirteen isolates, both positive and negative for specific IMP β-lactamases. The positive isolates included samples of the DNA templates for IMP1, IMP4, IMP7, IMP8, IMP14, IMP18, IMP27, and IMP35 described above. The RT-PCR assay included TaqMan™ reagents and an Applied Biosystems 7500 Fast Real-Time PCR system having cycling conditions of one cycle of at a temperature of about 98° C. for about 30 seconds followed by 30 cycles having a first duration of about 5 seconds at a temperature of about 98° C., a second duration of about 10 seconds at a temperature of about 60° C., and a third duration of about 20 seconds at a temperature of about 72° C. Results are shown in FIGS. 3 through 8, where the charts are provided as delta Rn (ΔRn) vs cycle. For instance, FIG. 3 shows a chart for amplification assisted with probe 1.1 in the first mixture, FIG. 4 shows a chart for amplification assisted with probe 1.2 in the first mixture, FIG. 5 shows a chart for amplification assisted with probe 1.3 in the first mixture, FIG. 6 shows a chart for amplification assisted with probe 2.1 in the second mixture, FIG. 7 shows a chart for amplification assisted with probe 2.2 in the second mixture, and FIG. 8 shows a chart for amplification assisted with probe 2.3 in the second mixture.

Unique family grouping between unrelated IMP β-lactamases were discovered using computer simulation and RAxML tree analysis, with a significant distance between groupings being defined as 0.05 Robinson-Foulds tree distances. Through in silico analysis it was determined that thirty two of forty eight IMP genes could be identified by both the first mixture and the second mixture of the first composition, that eight of the forty eight IMP genes were identified by the first mixture of the first composition alone, and that ten of the forty eight IMP genes were identified by the second mixture of the first composition alone. The simulated IMP genetic families were confirmed by RT-PCR and defined using probes (e.g., TaqMan™ probes). The RT-PCR assay described above provided in vitro analysis indicating that the first mixture detects six of the eight IMP genes (i.e., IMP1, IMP4, IMP7, IMP8, IMP18, and IMP27), the second mixture detects seven of the eight genes (i.e., IMP1, IMP4, IMP7, IMP8, IMP14, IMP18, and IMP35), and the both mixes together detected all eight isolates (i.e., IMP1, IMP4, IMP7, IMP8, IMP14, IMP18, IMP27, and IMP35). The assay as tested had 100% similarity and specificity.

A real time polymerase chain reaction (RT-PCR) assay was performed to analyze the detection performance of the second composition using the DNA templates for IMP1, IMP4, IMP7, IMP8, IMP14, IMP18, IMP27, and IMP35. The RT-PCR assay included EvaGreen™ reagents and an Applied Biosystems 7500 Fast Real-Time PCR system having cycling conditions of one cycle of at a temperature of about 98° C. for about 30 seconds followed by 30 cycles having a first duration of about 30 seconds at a temperature of about 98° C., a second duration of about 30 seconds at a temperature of about 60° C., and a third duration of about 30 seconds at a temperature of about 72° C. The first mixture of the second composition successfully detected IMP1, IMP4, IMP7, IMP8, IMP18, and IMP27. Detection was represented by a positive signal for an IMP carbapenemase generated by the first mixture. The second mixture of the second composition successfully detected IMP1, IMP4, IMP7, IMP8, IMP14, IMP18, and IMP35. Detection was represented by a positive signal for an IMP carbapenemase generated by the second mixture. Therefore, the first and second mixtures together successfully detected each of the eight DNA isolates representing seven of the sixteen defined groups of IMP variants.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

---

The invention claimed is:

1. A method comprising:

introducing a DNA-containing sample to a first mixture and to a second mixture, the first mixture including a first plurality of primer sets, wherein the first plurality of primer sets includes a first primer comprising the nucleotide sequence of SEQ ID NO:1, a second primer comprising the nucleotide sequence of SEQ ID NO:2, a third primer comprising the nucleotide sequence of SEQ ID NO:3, a fourth primer comprising the nucleotide sequence of SEQ ID NO:4, a fifth primer comprising the nucleotide sequence of SEQ ID NO:5, and a sixth primer comprising the nucleotide sequence of SEQ ID NO:6 first mixture, the second mixture including a second plurality of primer sets differing from the first plurality of primer sets, at least one of the first mixture and the second mixture including a fluorescent dye;

performing a multiplex polymerase chain reaction over multiple cycles with the DNA-containing sample and each of the first mixture and the second mixture; and detecting fluorescence resulting from the multiplex polymerase chain reaction for each cycle of the multiple cycles.

2. The method of claim 1, wherein the second plurality of primer sets includes a first primer comprising the nucleotide sequence of SEQ ID NO:10 and a second primer comprising the nucleotide sequence of SEQ ID NO:11.

3. The method of claim 2, wherein the second plurality of primer sets further includes a third primer comprising the nucleotide sequence of SEQ ID NO:12 and a fourth primer comprising the nucleotide sequence of SEQ ID NO:13.

4. The method of claim 3, wherein the second plurality of primer sets further includes a fifth primer comprising the nucleotide sequence of SEQ ID NO:14 and a sixth primer comprising the nucleotide sequence of SEQ ID NO:15.

5. The method of claim 1, wherein the first mixture includes a first plurality of probes, and wherein the second mixture includes a second plurality of probes differing from the first plurality of probes.

6. The method of claim 5, wherein the first plurality of probes includes a first probe comprising the nucleotide sequence of SEQ ID NO:7, a second probe comprising the nucleotide sequence of SEQ ID NO:8, and a third probe comprising the nucleotide sequence of SEQ ID NO:9.

7. The method of claim 6, wherein the second plurality of probes includes a first probe comprising the nucleotide sequence of SEQ ID NO:16, a second probe comprising the nucleotide sequence of SEQ ID NO:17, and a third probe comprising the nucleotide sequence of SEQ ID NO:18.

8. The method of claim 1, wherein the first mixture includes the fluorescent dye.

9. The method of claim 8, wherein the second mixture includes the fluorescent dye.

10. The method of claim 1, wherein detecting fluorescence resulting from the multiplex polymerase chain reaction for each cycle of the multiple cycles includes detecting fluorescence resulting from the multiplex polymerase chain reaction for each cycle of the multiple cycles in real time.

\* \* \* \* \*

SEQUENCE LISTING

```
Sequence total quantity: 18
SEQ ID NO: 1            moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 1
acgggtggaa tagagtggc                                                  19

SEQ ID NO: 2            moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 2
gcggactttg gccaagctt                                                  19

SEQ ID NO: 3            moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 3
gtagcattac tgccgcagg                                                  19

SEQ ID NO: 4            moltype = DNA  length = 19
FEATURE                 Location/Qualifiers
misc_feature            1..19
                        note = Synthetic Construct
source                  1..19
                        mol_type = other DNA
                        organism = synthetic construct
SEQUENCE: 4
taaccgcgct ccacaaacc                                                  19

SEQ ID NO: 5            moltype = DNA  length = 19
FEATURE                 Location/Qualifiers
misc_feature            1..19
                        note = Synthetic Construct
source                  1..19
                        mol_type = other DNA
```

```
                            organism = synthetic construct
SEQUENCE: 5
gggcggaata gagtggctt                                                19

SEQ ID NO: 6            moltype = DNA   length = 19
FEATURE                 Location/Qualifiers
misc_feature            1..19
                        note = Synthetic Construct
source                  1..19
                        mol_type = other DNA
                        organism = synthetic construct
SEQUENCE: 6
tttggcggac tctggccaa                                                19

SEQ ID NO: 7            moltype = DNA   length = 24
FEATURE                 Location/Qualifiers
variation               1..24
                        note = Synthetic Construct. N at position 14 is either C or
                        T.
variation               14
                        note = n is a, c, g, or t
source                  1..24
                        mol_type = other DNA
                        organism = synthetic construct
SEQUENCE: 7
cgtagtggtt tggntacctg aaaa                                          24

SEQ ID NO: 8            moltype = DNA   length = 26
FEATURE                 Location/Qualifiers
misc_feature            1..26
                        note = Synthetic Construct
source                  1..26
                        mol_type = other DNA
                        organism = synthetic construct
SEQUENCE: 8
aagcttgaag aaggtgtttt gttcat                                        26

SEQ ID NO: 9            moltype = DNA   length = 23
FEATURE                 Location/Qualifiers
misc_feature            1..23
                        note = Synthetic Construct
source                  1..23
                        mol_type = other DNA
                        organism = synthetic construct
SEQUENCE: 9
cccacgtatg cgtctgaatt aac                                           23

SEQ ID NO: 10           moltype = DNA   length = 19
FEATURE                 Location/Qualifiers
misc_feature            1..19
                        note = Synthetic Construct
source                  1..19
                        mol_type = other DNA
                        organism = synthetic construct
SEQUENCE: 10
gaagcttggc caaagtccg                                                19

SEQ ID NO: 11           moltype = DNA   length = 19
FEATURE                 Location/Qualifiers
misc_feature            1..19
                        note = Synthetic Construct
source                  1..19
                        mol_type = other DNA
                        organism = synthetic construct
SEQUENCE: 11
accctttaac cgcctgctc                                                19

SEQ ID NO: 12           moltype = DNA   length = 19
FEATURE                 Location/Qualifiers
misc_feature            1..19
                        note = Synthetic Construct
source                  1..19
                        mol_type = other DNA
                        organism = synthetic construct
SEQUENCE: 12
cacggcttgg tggttcttg                                                19

SEQ ID NO: 13           moltype = DNA   length = 19
FEATURE                 Location/Qualifiers
```

```
misc_feature        1..19
                    note = Synthetic Construct
source              1..19
                    mol_type = other DNA
                    organism = synthetic construct
SEQUENCE: 13
cgttatctgg agtgtgccc                                                19

SEQ ID NO: 14       moltype = DNA  length = 19
FEATURE             Location/Qualifiers
misc_feature        1..19
                    note = Synthetic Construct
source              1..19
                    mol_type = other DNA
                    organism = synthetic construct
SEQUENCE: 14
cacggcttgg tggttcttg                                                19

SEQ ID NO: 15       moltype = DNA  length = 19
FEATURE             Location/Qualifiers
misc_feature        1..19
                    note = Synthetic Construct
source              1..19
                    mol_type = other DNA
                    organism = synthetic construct
SEQUENCE: 15
tatcctgagt gtgccctgg                                                19

SEQ ID NO: 16       moltype = DNA  length = 25
FEATURE             Location/Qualifiers
misc_feature        1..25
                    note = Synthetic Construct
source              1..25
                    mol_type = other DNA
                    organism = synthetic construct
SEQUENCE: 16
aaatatggta aggcaaaact ggttg                                         25

SEQ ID NO: 17       moltype = DNA  length = 25
FEATURE             Location/Qualifiers
misc_feature        1..25
                    note = Synthetic Construct
source              1..25
                    mol_type = other DNA
                    organism = synthetic construct
SEQUENCE: 17
ggaatagagt ggcttaattc tcaat                                         25

SEQ ID NO: 18       moltype = DNA  length = 25
FEATURE             Location/Qualifiers
misc_feature        1..25
                    note = Synthetic Construct
source              1..25
                    mol_type = other DNA
                    organism = synthetic construct
SEQUENCE: 18
tcaaaggcag tatttcctca cattt                                         25
```